US010993704B2

(12) United States Patent
Choi

(10) Patent No.: US 10,993,704 B2
(45) Date of Patent: May 4, 2021

(54) SYSTEM AND METHOD FOR CALIBRATION OF MECHANICAL THREE-DIMENSIONAL ULTRASOUND PROBE

(71) Applicant: Verathon Inc., Bothell, WA (US)

(72) Inventor: Joon Hwan Choi, Bothell, WA (US)

(73) Assignee: Verathon Inc., Bothell, WA (US)

( * ) Notice: Subject to any disclaimer, the term of this patent is extended or adjusted under 35 U.S.C. 154(b) by 424 days.

(21) Appl. No.: 16/131,315

(22) Filed: Sep. 14, 2018

(65) Prior Publication Data
US 2019/0090858 A1 Mar. 28, 2019

Related U.S. Application Data

(60) Provisional application No. 62/562,613, filed on Sep. 25, 2017.

(51) Int. Cl.
*A61B 8/00* (2006.01)
*A61B 8/14* (2006.01)
*A61B 8/08* (2006.01)

(52) U.S. Cl.
CPC ............ *A61B 8/587* (2013.01); *A61B 8/4461* (2013.01); *A61B 8/483* (2013.01); *A61B 8/5269* (2013.01); *A61B 8/145* (2013.01); *A61B 8/4494* (2013.01); *A61B 8/469* (2013.01)

(58) Field of Classification Search
CPC ....... A61B 8/587; A61B 8/5269; A61B 8/483; A61B 8/4461; A61B 8/469; A61B 8/4494; A61B 8/145
See application file for complete search history.

(56) References Cited

U.S. PATENT DOCUMENTS

| 3,665,379 | A | 5/1972 | Trott |
| 3,857,052 | A | 12/1974 | Beller |
| 4,081,216 | A | 3/1978 | Cook |
| 4,187,488 | A | 2/1980 | Anderson et al. |
| 4,286,455 | A | 9/1981 | Ophir et al. |
| 4,331,021 | A | 5/1982 | Lopez et al. |
| 4,417,582 | A | 11/1983 | Trimmer et al. |
| 4,453,408 | A | 6/1984 | Clayman |
| 4,838,070 | A | 6/1989 | Bradley |
| 4,843,866 | A | 7/1989 | Madsen et al. |
| 4,903,523 | A | 2/1990 | Flynn |
| 4,959,992 | A | 10/1990 | Gentles |
| 5,054,310 | A | 10/1991 | Flynn |
| 5,327,771 | A | 7/1994 | Gentles |
| 5,433,102 | A | 7/1995 | Pedziwiatr |

(Continued)

*Primary Examiner* — Daniel Pihulic
(74) *Attorney, Agent, or Firm* — Snyder, Clark, Lesch & Chung, LLP

(57) ABSTRACT

A method for calibrating an ultrasound probe includes receiving, from the ultrasound probe, data of a target within a test fixture, wherein the target includes a repetitive pattern along two axes; generating a first ultrasound image of the target; and identifying distortion of the target in the first ultrasound image. The method also includes estimating, based on identifying the distortion, offset parameter values for one or more of three angular errors within the ultrasound probe; generating a second ultrasound image of the target using the offset parameter values; identifying corrected distortion of the target in the second ultrasound image; and storing the offset parameter values.

20 Claims, 12 Drawing Sheets

(56) References Cited

U.S. PATENT DOCUMENTS

| | | |
|---|---|---|
| 5,463,593 A | 10/1995 | Zanelli et al. |
| 5,530,678 A | 6/1996 | Kosalos |
| 5,574,212 A | 11/1996 | Madsen et al. |
| 5,625,137 A | 4/1997 | Madsen et al. |
| 5,699,806 A | 12/1997 | Webb et al. |
| 5,756,875 A | 5/1998 | Parker et al. |
| 5,827,942 A | 10/1998 | Madsen et al. |
| 6,138,495 A | 10/2000 | Paltieli et al. |
| 6,238,343 B1 | 5/2001 | Madsen et al. |
| 6,311,540 B1 | 11/2001 | Paltieli et al. |
| 6,635,486 B2 | 10/2003 | Madsen et al. |
| 6,664,404 B2 | 12/2003 | Jackson |
| 6,829,929 B2 | 12/2004 | Palmer et al. |
| 6,883,362 B2 | 4/2005 | Ogawa |
| 7,090,639 B2 | 8/2006 | Govari |
| 7,748,252 B2 | 7/2010 | Wieringa et al. |
| 7,874,987 B2 | 1/2011 | Altmann et al. |
| 7,996,057 B2 | 8/2011 | Govari et al. |
| 8,000,442 B2 | 8/2011 | Lachaine et al. |
| 8,036,063 B2 | 10/2011 | Smith et al. |
| 8,887,552 B2 | 11/2014 | Madsen et al. |
| 2004/0254458 A1 | 12/2004 | Govari |
| 2008/0214936 A1 | 9/2008 | Wieringa et al. |
| 2019/0090858 A1* | 3/2019 | Choi .................... A61B 8/5269 |

* cited by examiner

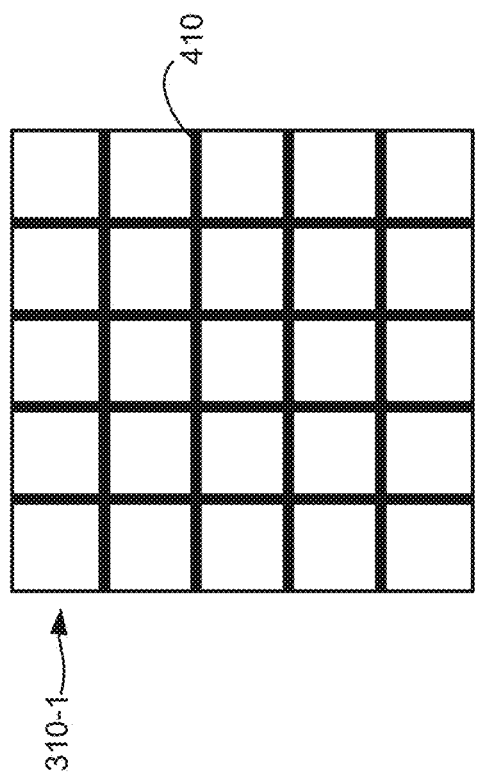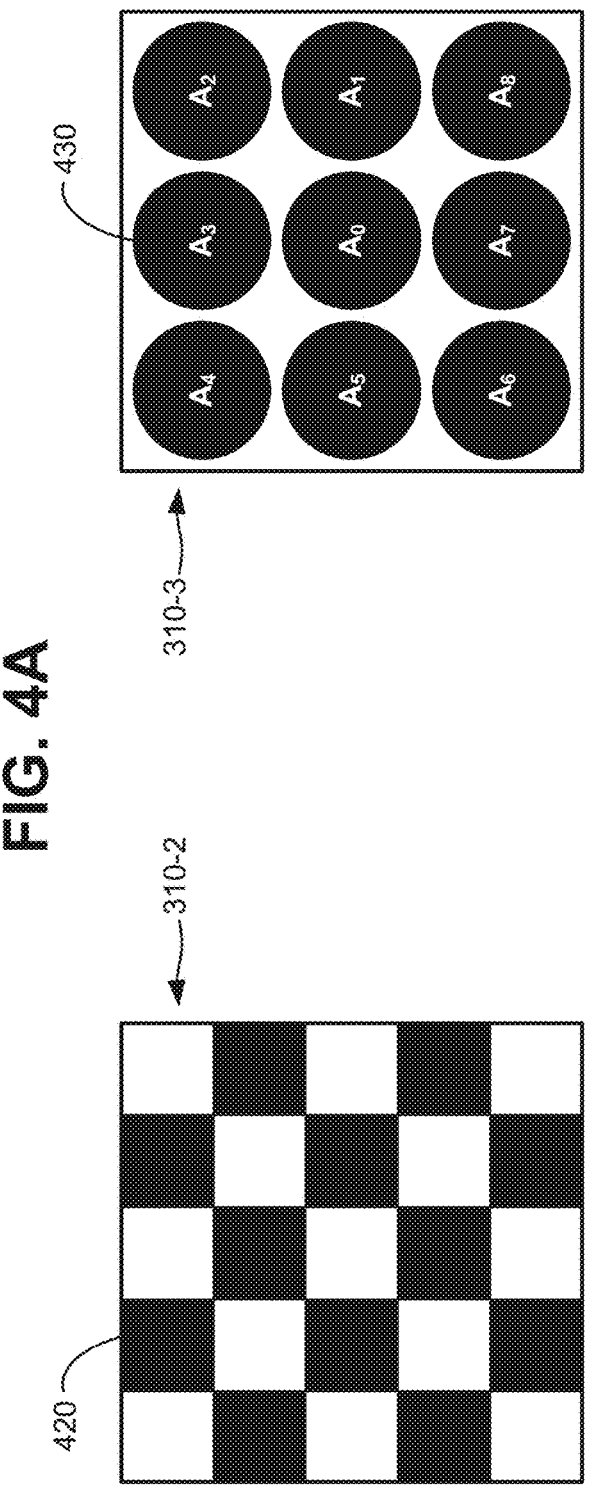

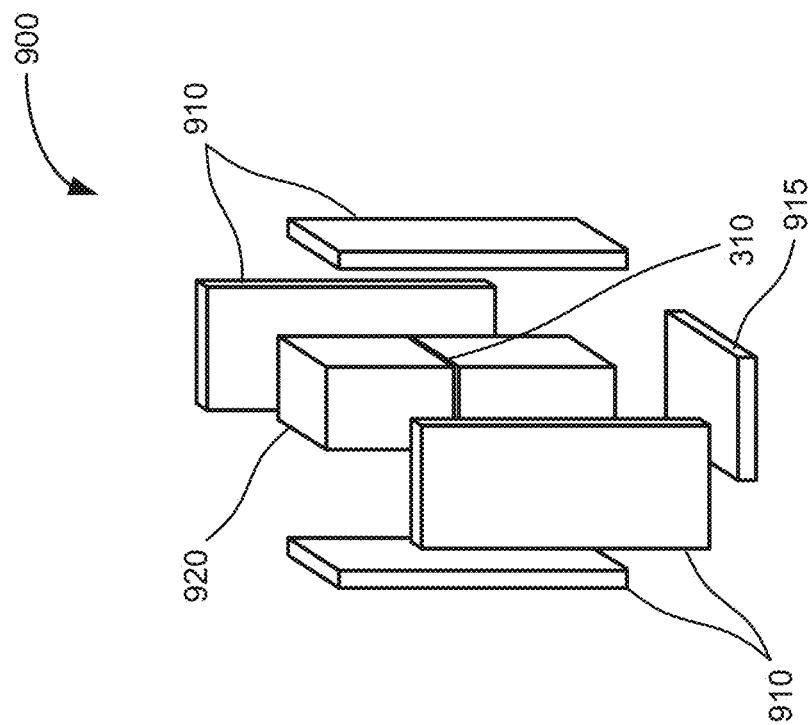
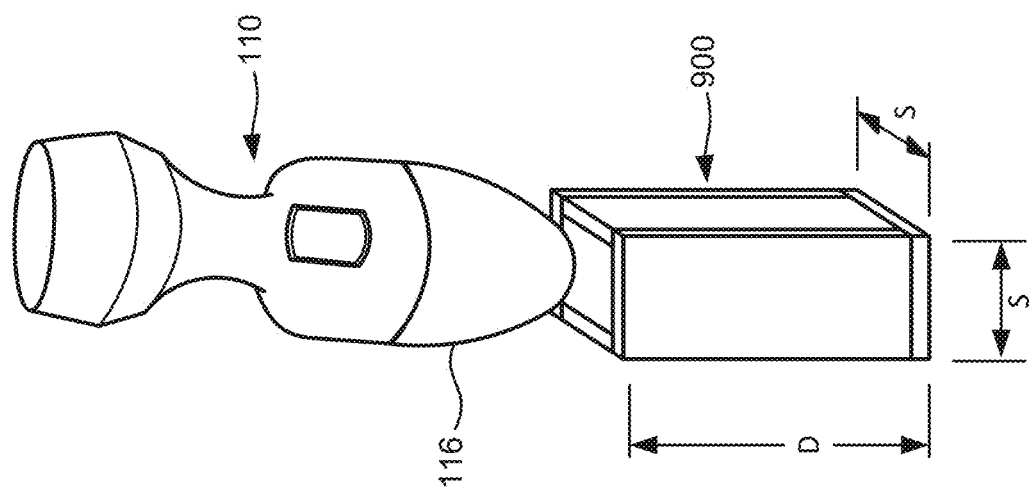
FIG. 9B
FIG. 9A

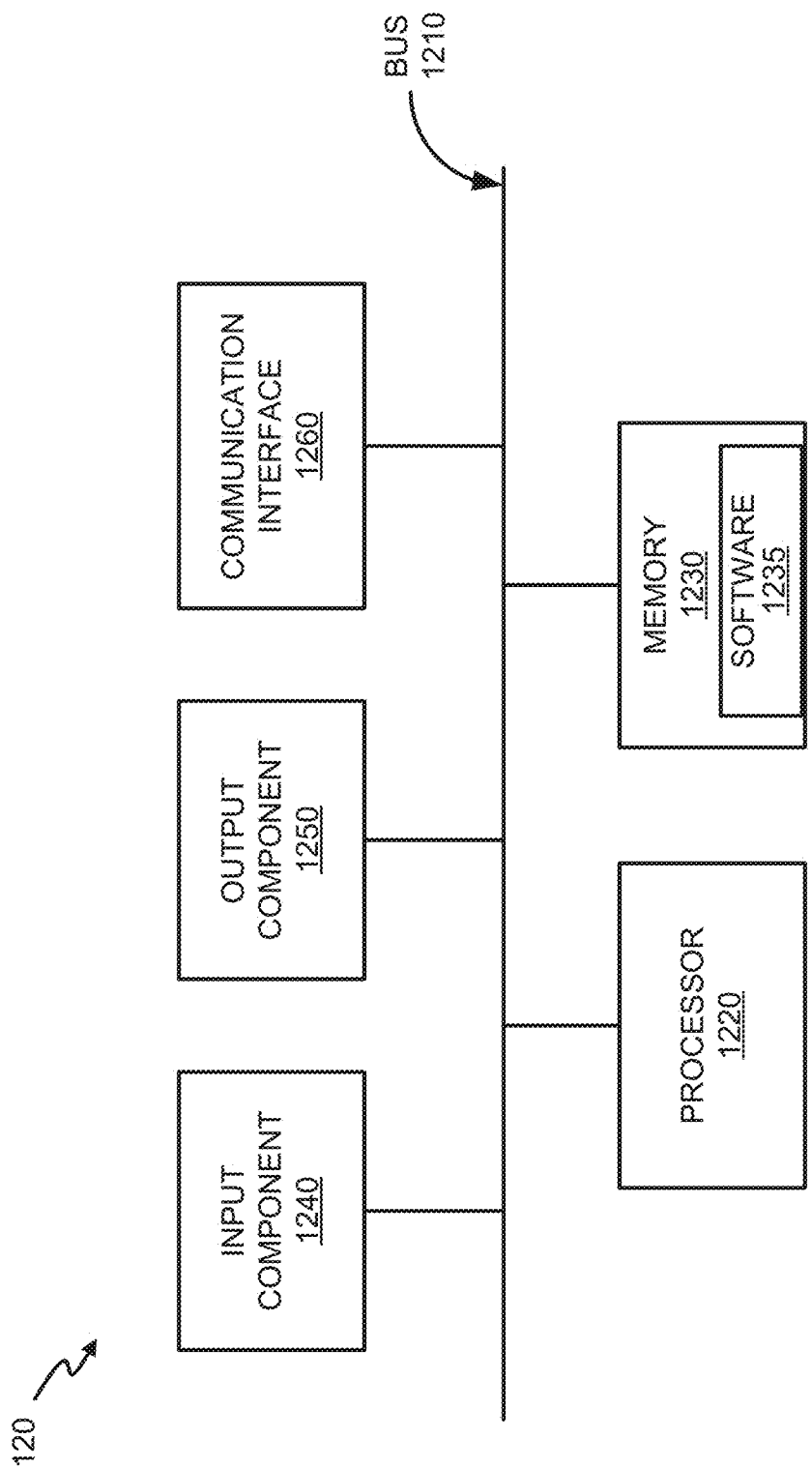

US 10,993,704 B2

SYSTEM AND METHOD FOR CALIBRATION OF MECHANICAL THREE-DIMENSIONAL ULTRASOUND PROBE

CROSS-REFERENCE TO RELATED APPLICATION

This application claims priority under 35 U.S.C. § 119, based on U.S. Provisional Patent Application No. 62/562,613 filed Sep. 25, 2017, the disclosure of which is hereby incorporated by reference.

BACKGROUND OF THE INVENTION

Ultrasound scanners are typically used to identify a target organ or other structures in the body and/or determine features associated with the target organ/structure, such as the size of the organ/structure or the volume of fluid in the organ. An ultrasound probe typically includes one or more ultrasound transducer elements that transmit ultrasound energy and receive acoustic reflections or echoes generated by internal structures/tissue within a body. These reflections or echoes may be converted into three-dimensional (3D) data. Errors in the probe mechanism, such as small mechanical assembly deviations, can distort the 3D ultrasound data. The distortion can adversely affect measurement of features associated with the target organ/structure.

BRIEF DESCRIPTION OF THE DRAWINGS

FIGS. 4A-4C are schematics illustrating exemplary ultrasound target patterns for the test fixture of FIG. 3;

FIGS. 9A and 9B are simplified diagrams illustrating a test fixture according to another implementation described herein;

FIG. 12 is a diagram illustrating exemplary components of a base unit in the system of FIG. 1.

DETAILED DESCRIPTION OF THE PREFERRED EMBODIMENTS

The following detailed description refers to the accompanying drawings. The same reference numbers in different drawings may identify the same or similar elements.

Implementations described herein relate to identification and compensation of errors in data from ultrasound probes. Errors in the probe mechanism, such as mechanical alignment errors during assembly, can cause distortion of 3D ultrasound data collected by the probe. This distortion can negatively affect measurements of scanned organs (e.g., bladder volume, aorta diameter, prostate width/height, etc.). One common way to check for distortion is a phantom variability test. For example, the volume of a bladder phantom can be measured multiple times by tilting a probe in several different directions. If the 3D data is spatially distorted, volume readings based on probe data would not be consistent between tilt directions. This variability test provides neither precise nor quantitative error estimates.

According to implementations described herein, systems and methods are provided to clearly visualize and/or analyze spatial distortion in 3D volume data, of a target grid, from a mechanical 3D ultrasound probe. Errors visible in the grid data can be measured precisely and subsequently compensated for to provide for accurate probe output. As described further herein, compensation for measured errors may be accomplished using either mechanical or software adjustments.

In one implementation, a method for calibrating an ultrasound probe may include receiving, from the ultrasound probe, 3D data of a target within a test fixture. The target may include a repetitive pattern along two axes. The method may also include generating a first ultrasound image of the target and identifying distortion of the target in the first ultrasound image. The method may further include estimating, based on identifying the distortion, offset parameter values for one or more of three angular errors within the ultrasound probe; generating a second ultrasound image of the target using the offset parameter values; identifying corrected distortion of the target in the second ultrasound image; and storing the offset parameter values.

Figure 1:
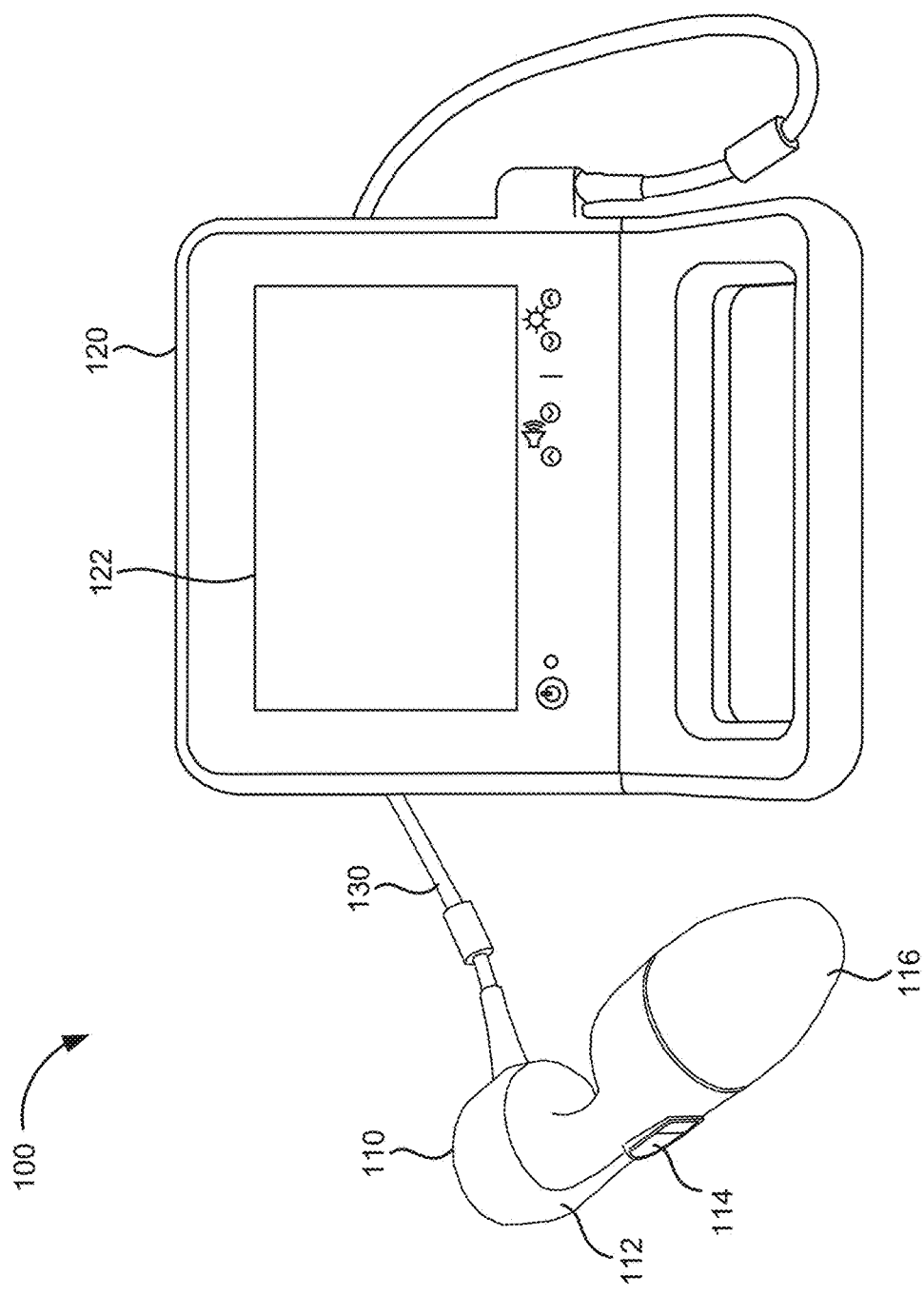
FIG. 1 is a schematic of a scanning system in which systems and methods described herein may be implemented.

FIG. 1 is a schematic of a scanning system 100 in which systems and methods described herein may be implemented. Referring to FIG. 1, scanning system 100 includes probe 110, base unit 120, and cable 130.

Probe 110 includes handle portion 112 (also referred to as handle 112), trigger 114 and nose portion 116 (also referred to as dome or dome portion 116). Medical personnel may hold probe 110 via handle 112 and press trigger 114 to activate one or more ultrasound transceivers and transducers located in nose portion 116 to transmit ultrasound signals toward the target organ of interest. For example, probe 110 may be positioned on a pelvic area of a patient and over a target organ of interest, such as the patient's bladder.

Handle 112 allows a user to move probe 110 relative to a patient (not shown). As discussed above, trigger 114 initiates an ultrasound scan of a selected anatomical portion while dome 116 is in contact with a surface portion of the patient when the selected anatomical portion is scanned. Dome 116 is typically formed of a material that provides an appropriate acoustical impedance match to the anatomical portion and/or permits ultrasound energy to be properly focused as it is projected into the anatomical portion.

Probe 110 may communicate with base unit 120 via a wired connection, such as via cable 130. In other implementations, probe 110 may communicate with base unit 120 via a wireless connection (e.g., Bluetooth, WiFi, etc.). In each case, base unit 120 includes display 122 to allow a user to view processed results from an ultrasound scan, and/or to allow operational interaction with respect to the user during operation of probe 110. For example, display 122 may include an output display/screen, such as a liquid crystal display (LCD), light emitting diode (LED) based display, or other type of display that provides text and/or image data to a user. For example, display 122 may provide instructions for positioning probe 110 relative to the selected anatomical portion of a patient. Display 122 may also display two-dimensional or three-dimensional images of the selected anatomical region. In some implementations, display 122 may include a graphical user interface (GUI) that allows the user to select various features associated with an ultrasound scan.

To scan a selected anatomical portion of a patient, dome 116 may be positioned against a surface portion of the patient that is proximate to the anatomical portion to be scanned. The user actuates the transceiver by depressing trigger 114. In response, the transducer elements optionally position the transceiver, which transmits ultrasound signals into the body, and receives corresponding return echo signals that may be at least partially processed by the transceiver to generate an ultrasound image of the selected anatomical portion. In a particular embodiment, system 100 transmits ultrasound signals in a range that extends from approximately about two megahertz (MHz) to approximately 10 or more MHz (e.g., 18 MHz).

In one embodiment, probe 110 may be coupled to a base unit 120 that is configured to generate ultrasound energy at a predetermined frequency and/or pulse repetition rate and to transfer the ultrasound energy to the transceiver. Base unit 120 also includes one or more processors or processing logic configured to process reflected ultrasound energy that is received by the transceiver to produce an image of the scanned anatomical region.

In still another particular embodiment, probe 110 may be a self-contained device that includes a microprocessor positioned within the probe 110 and software associated with the microprocessor to operably control the transceiver, and to process the reflected ultrasound energy to generate the ultrasound image. Accordingly, a display on probe 110 may be used to display the generated image and/or to view other information associated with the operation of the transceiver. For example, the information may include alphanumeric data that indicates a preferred position of the transceiver prior to performing a series of scans. In other implementations, the transceiver may be coupled to a general-purpose computer, such as a laptop or a desktop computer that includes software that at least partially controls the operation of the transceiver, and also includes software to process information transferred from the transceiver so that an image of the scanned anatomical region may be generated.

Figure 2:
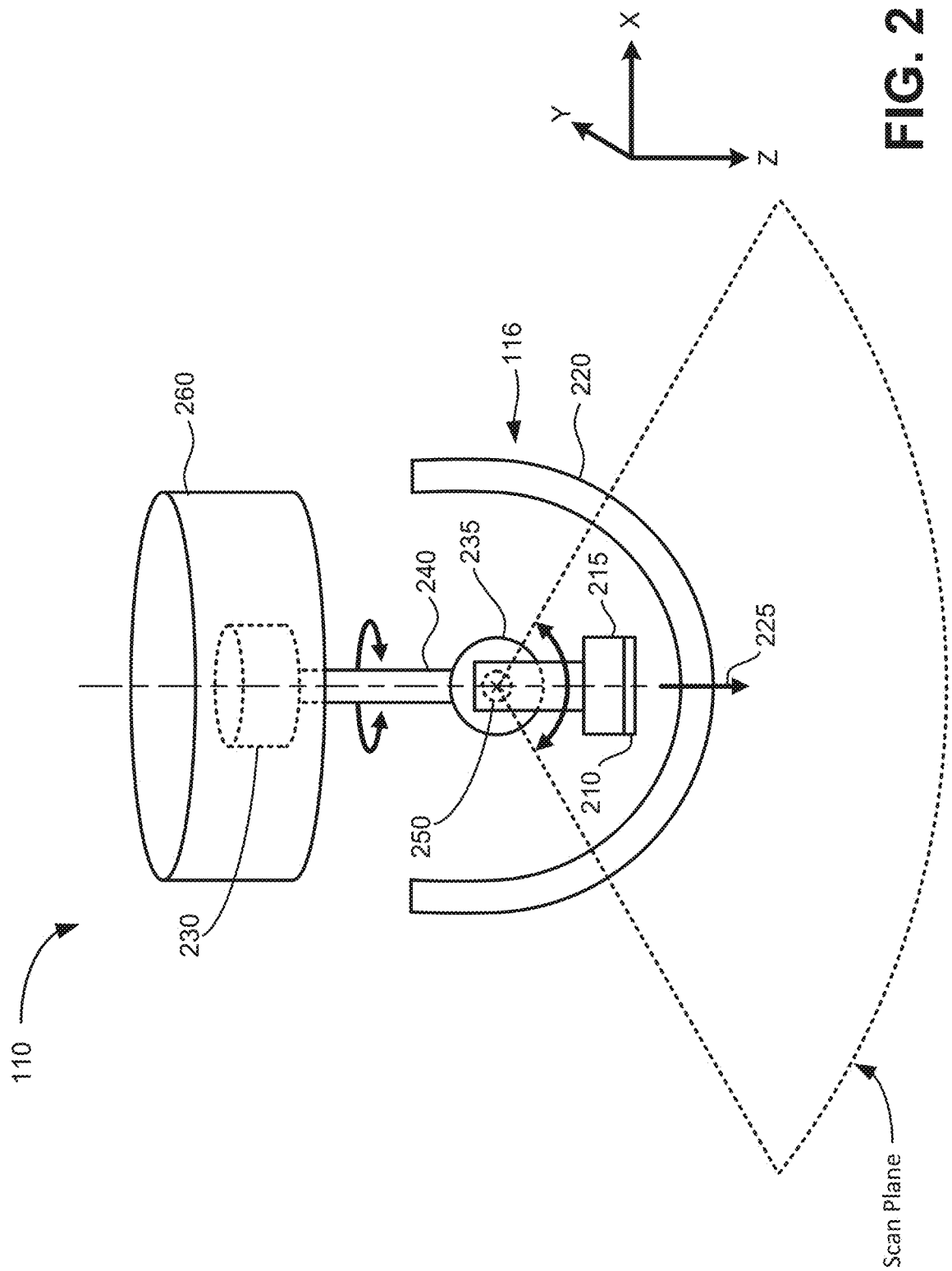
FIG. 2 is a schematic of a portion of the probe of FIG. 1 in an exemplary implementation.

FIG. 2 is a schematic of an internal portion of probe 110 in an exemplary implementation. In the example of FIG. 2, probe 110 is configured to obtain 3D image data. Generally, probe 110 includes one or more ultrasound transceiver elements and one or more transducer elements within dome 116 that transmit ultrasound energy outwardly from dome 116, and receive acoustic reflections or echoes generated by internal structures/tissue within an anatomical portion. Referring to FIG. 2, probe 110 includes a transducer 210 connected to a base 260. The elements illustrated in FIG. 2 may be included within dome portion 116 of probe 110.

Transducer 210 may transmit ultrasound signals from probe 110 through a wall 220 of dome portion 116, indicated by reference 225 in FIG. 2. Transducer 210 may be mounted to a transducer bucket 215, which in turn is mounted to base 260 to allow transducer 210 to rotate about two perpendicular axes. A motor 230 may be included to move a first axis or spine 240, and another motor 235 may be included to move a second axis or shaft 250. For example, transducer 210 may rotate around first axis 240 with respect to base 260 and rotate around a second axis 250 with respect to base 260. The first axis 240, extending in a generally longitudinal direction of probe 110, is referred to herein as the theta ($\theta$) axis. The second axis 250, extending in a direction orthogonal to first axis 240, is referred to herein as the phi ($\phi$) axis. In an exemplary implementation, the range of theta and phi motion may be less than 180 degrees. In one implementation, the scanning may be interlaced with respect to the theta motion and phi motion. For example, movement of transducer 210 may occur in the theta direction followed by movement in the phi direction. This enables probe 110 to obtain smooth continuous volume scanning as well as improving the rate at which the scan data is obtained.

While a single transducer is shown in the implementation of FIG. 2, different configurations for probe 110 may be used. For example, the one or more ultrasound transducer elements may include a one-dimensional, two-dimensional, or annular array of piezoelectric elements that may be moved within dome 116 by a motor to provide different scan directions with respect to the transmission of ultrasound signals by the transceiver elements. Alternatively, the transducer elements may be stationary with respect to probe 110 so that the selected anatomical region may be scanned by selectively energizing the elements in the array.

Referring to FIG. 2, production/mechanical alignment errors in the manufacture of probe 110 can result in various types of calibration errors. Errors may be related to attachment of transducer 210 to transducer bucket 215. For example, attachment of transducer 210 to transducer bucket 215 may result in a non-parallel interface (e.g., tilt), where transducer 210 may be tilted with respect to transducer bucket 215. As another example, transducer 210 may not be properly aligned along axis 240 when attached to transducer bucket 215. Additionally, or alternatively, errors may be related to attachment of transducer bucket 215 to axis 250. For example, transducer bucket 215 may not be aligned with axis 240, may be rotated with respect to axis 240, or may be tilted with respect to axis 240. Similar production/mechanical alignment errors may occur in the attachment of spine 240 to motor 230, or the attachment of motor 230 within base 260. A complete error model to identify and correct for each source of error would be computationally intensive.

In the example of FIG. 2, an x axis is a horizontal axis parallel to the scan plane, a y axis is another horizontal axis orthogonal to the x axis; and a z axis is a vertical axis in the direction of depth. According to an implementation, angular errors (E) inside probe 110 can be approximated as the combination of three sources: a theta offset ($E_\theta$) associated with theta axis 240, a phi offset ($E_\phi$) associated with phi axis 250, and a perpendicular offset ($E_p$) associated with a skew angle perpendicular to the scan plane. The theta offset may result when the actual rotational angle about theta axis 240 differs from the expected or sensed rotational angle (due to small assembly deviations, for example). For example, internal logic of probe 110 may indicate an angular rotation of 90 degrees about theta axis 240 when the actual angular rotation is actually 89 degrees. The phi offset may result when the actual rotational angle about phi axis 250 differs from the expected or sensed rotational angle (e.g., also due to small assembly deviations). The perpendicular offset may result when the B-mode scan plane is not orthogonal to the base 230 (e.g., transducer 210 may not be mounted flush against the bottom surface of transducer bucket 215, bucket 215 may be misaligned, axis 240 and motor 230 may be misaligned, etc.)

When error parameters for theta rotation, perpendicular offset, and phi rotation are given, an actual scanline direction for θ and φ is:

$$R(u_z, \theta+E_\theta) \cdot R(u_x, E_p) \cdot R(u_y, \phi+E_\phi) \cdot u_z,$$

where $u_x$, $u_y$, and $u_z$ represents the unit vector along the x, y and z axes (of FIG. 2), respectively. $R(u, \psi)$ is the rotation matrix by $\psi$ about an axis in the direction of U:

$$R(u, \psi) = \begin{bmatrix} \cos\psi + u_x^2(1-\cos\psi) & u_x u_y(1-\cos\psi) - u_z\sin\psi & u_x u_z(1-\cos\psi) + u_y\sin\psi \\ u_y u_x(1-\cos\psi) + u_z\sin\psi & \cos\psi + u_y^2(1-\cos\psi) & u_y u_z(1-\cos\psi) - u_x\sin\psi \\ u_z u_x(1-\cos\psi) - u_y\sin\psi & u_z u_y(1-\cos\psi) + u_x\sin\psi & \cos\psi + u_z^2(1-\cos\psi) \end{bmatrix}$$

Thus, theta offset ($E_\theta$), perpendicular offset ($E_p$), and phi offset ($E_\phi$) may each be estimated in the above error model and used to compensate for the most common mechanical alignment errors in probe 110.

Figure 3:
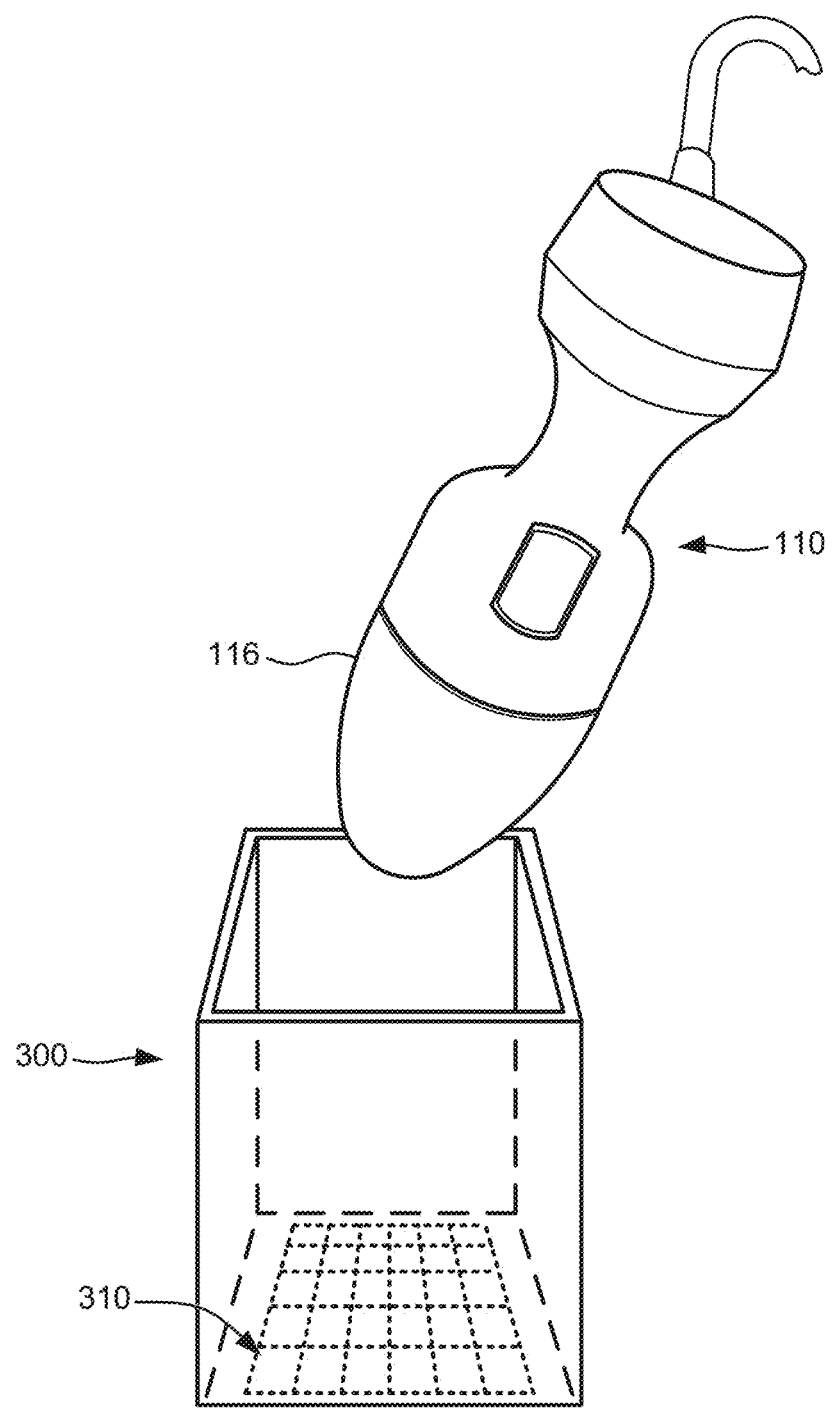
FIG. 3 is a schematic illustrating a test fixture with an ultrasound target according to an implementation described herein.

FIG. 3 is a schematic illustrating a test fixture 300 with an ultrasound target 310 for probe 110, according to an implementation described herein. Test fixture 300 may be filled with a fluid or solid test material, such as water, rubber, or a tissue-like material (not shown in FIG. 3), and target 310 may rest below or within the test material. Target 310 may generally provide a grid shape or another pattern of a material that has distinctive echo characteristics from the test material. For example, if the test material is water or another hypoechoic material, target 310 may include a hyperechoic material that reflects ultrasonic energy or waves and allows for easy visualization of spatial distortion. Conversely, if the test material is a hyperechoic material, target 310 may include a hypoechoic material.

FIGS. 4A-4C provide examples of targets 310. Target 310-1 in FIG. 4A includes a grid 410 of straight lines. In one implementation, grid 410 may be an echo-reflecting material within an acoustically transparent material. Target 310-2 in FIG. 4B includes a checkerboard pattern 420 with alternating transparent squares (shown as un-filled) and echo-reflecting squares (shown as filled black squares). Target 310-3 in FIG. 4C includes a pattern of echo-reflecting circles 430. Targets 310 may be positioned within test fixture 300 such that a pattern (e.g., grid 410, checkerboard pattern 420, circles 430, etc.) is aligned with sides of the test fixture 300. For example, grid 410 may be installed in test fixture 300 with lines of grid 410 parallel and perpendicular to edges of test fixture 300.

Figure 5A:
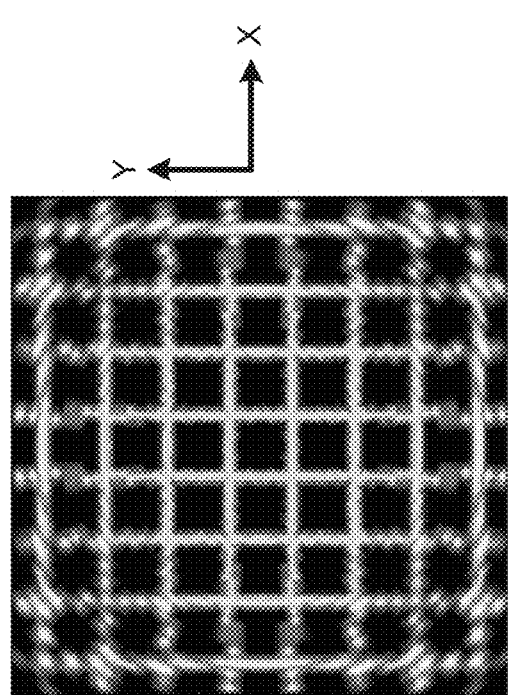
FIGS. 5A-5D are examples of ultrasound test images using the target pattern of FIG. 4A.
Figure 5D:
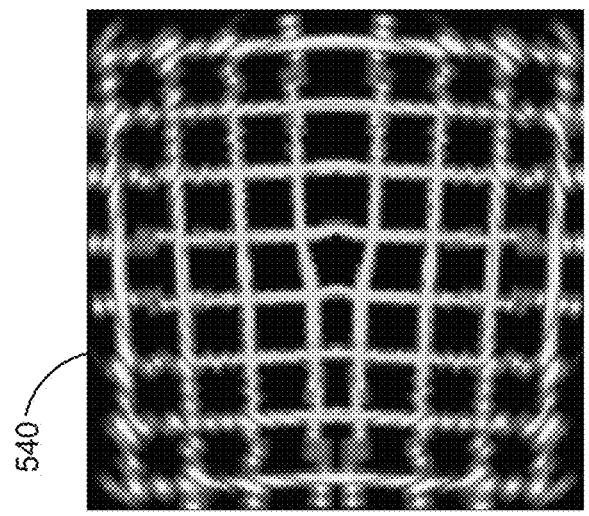
Figure 5C:
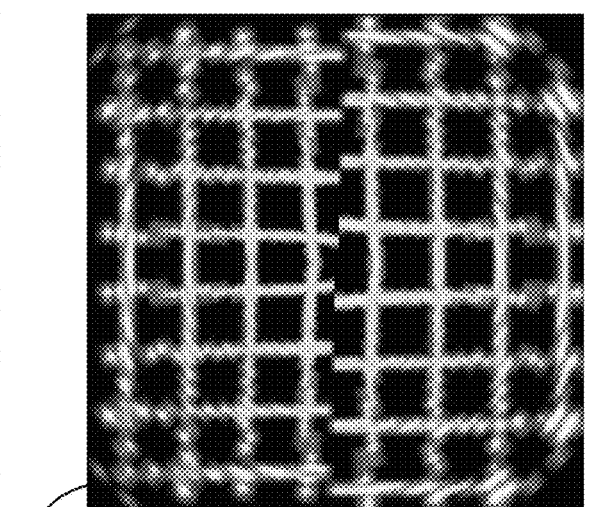
Figure 5B:
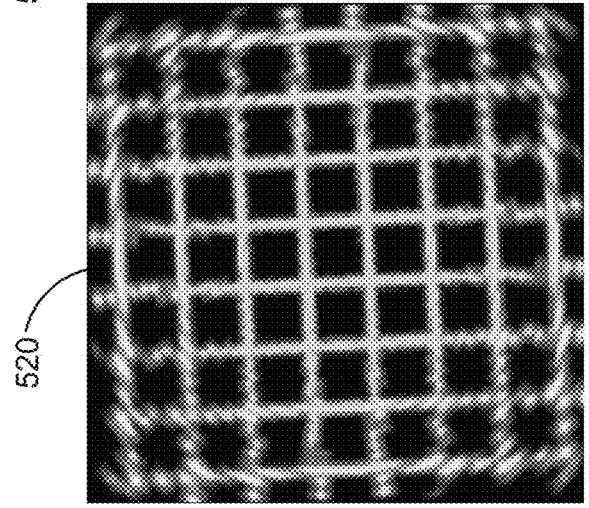

FIGS. 5A-5D are simulated ultrasound images of target 310-1. Each of FIGS. 5A-5D represent cross-sectional images (typically referred to as C-mode images, which are perpendicular to typical B-mode images) generated from the 3D ultrasound data at the depth of grid target 310-1. The horizontal line crossing the center of the image (i.e., the x axis) corresponds to a first scan plane (i.e., theta angle around theta axis 240 equals 0 degrees), and the y axis corresponds to the plane where the theta angle equals 90 degrees. FIG. 5A is an image 510 with no error. FIG. 5B is an image 520 showing an inaccurate theta angle around theta axis 240, or theta offset ($E_\theta$). FIG. 5C is an image 530 showing an inaccurate phi angle around phi axis 250, or phi offset ($E_\phi$). FIG. 5D is an image 540 showing a skewed transducer mechanism that is not perpendicular to the intended scan plane, or having a perpendicular offset ($E_p$).

Each of images 510-540 may include distinctive characteristics that permit a user or software to identify a likely cause of error. Image 510 may indicate correct alignment with no error because lines (or patterns) in the central portion of the grid in image 510 are parallel and aligned vertically/horizontally. Image 520 indicates an inaccurate theta angle because lines (or patterns) in the central portion of the grid in image 520 are rotated slightly from a true vertical/horizontal orientation. The orientation of asymmetry in images 530 and 540 may be used to distinguish phi error from perpendicular error. For example, when the first scan plane is aligned with the x axis (i.e., theta angle around theta axis 240 equals 0 degrees), a phi error makes either the upper or lower half expanded/contracted, with a possible discontinuity, as shown in image 530. On the other hand, perpendicular error makes either the left or right half expanded/contracted as shown in image 540.

Figure 6:
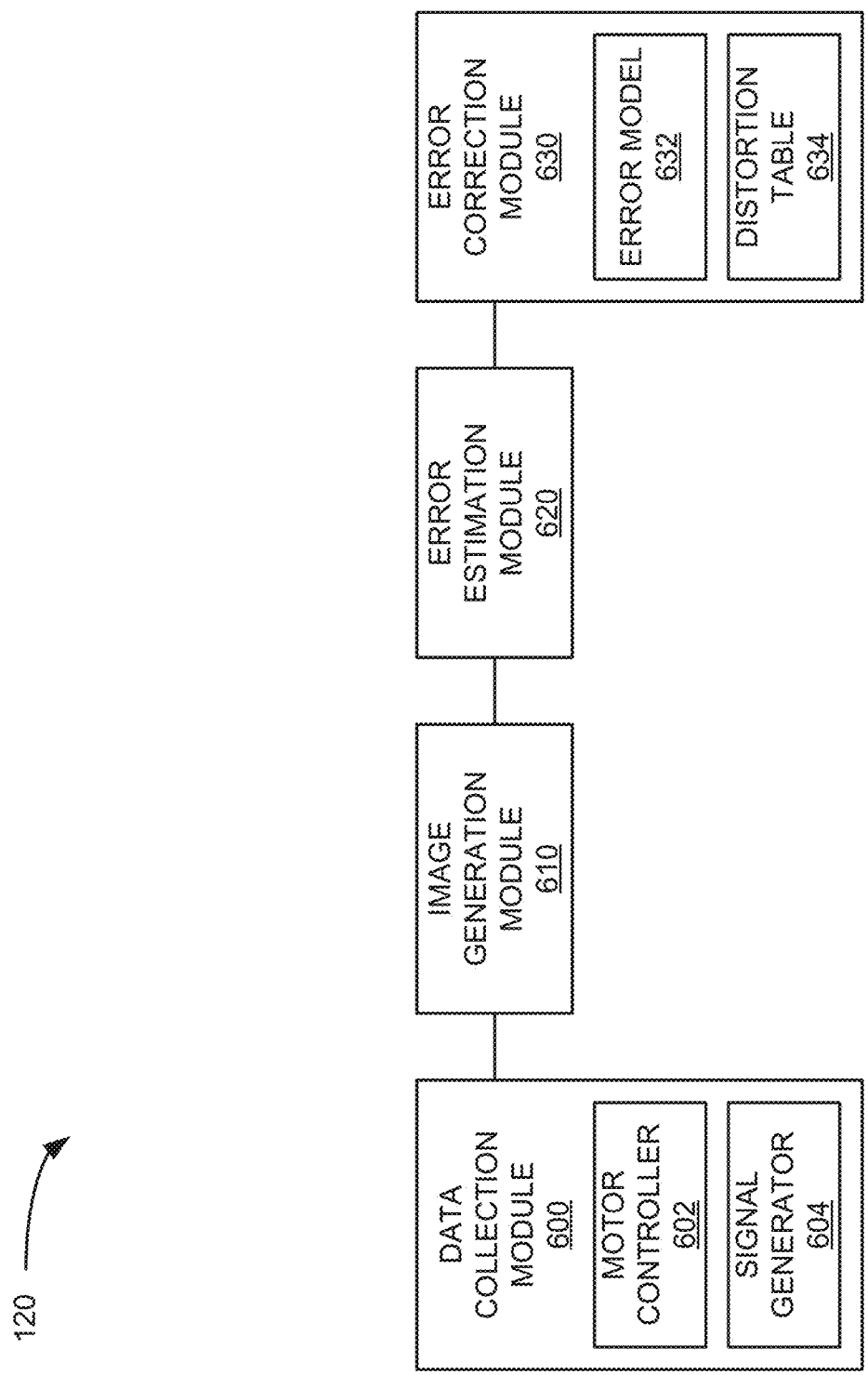
FIG. 6 is a block diagram of functional logic components of the system of FIG. 1 in accordance with an exemplary implementation.

FIG. 6 is a block diagram of functional logic components implemented in system 100 in accordance with an exemplary implementation. Referring to FIG. 6, system 100 includes a data collection module 600, an image generation module 610, an error estimation module 620, and an error correction module 630. In an exemplary implementation, data collection module 600 may be part of probe 110 and the other functional units (e.g., image generation module 610, error estimation module 620, and an error correction module 630) may be implemented in base unit 120. In other implementations, the particular units and/or logic may be implemented entirely within a single device or by other devices, such as via computing devices or servers located externally with respect to both probe 110 and base unit 120 (e.g., accessible via a wireless connection to the Internet or to a local area network within a hospital, etc.). For example, probe 110 may transmit echo data and/or image data to a processing system via, for example, a wireless connection (e.g., WI-FI or some other wireless protocol/technology) that is located remotely from probe 110 and base unit 120.

Data collection module 600 obtains data associated with multiple scan planes corresponding to a region of interest or, in a testing/calibration context, a target (e.g., target 310). For example, data collection module 600 may receive and process echo data to generate two-dimensional (2D) B-mode image data. In other implementations, data collection module 600 may receive echo data that is processed to generate 3D image data.

In one implementation, data collection module 600 may include a motor controller 602 and a signal generator 604. Motor controller 602 may provide angular rotation commands for motor 230 and motor 235 and may monitor a corresponding angular position of spine 240 and shaft 250. In one aspect, motor controller 602 may incorporate angular error values to compensate for mechanical alignment errors in probe 110. For example, motor controller 602 may incorporate offset values to angular commands after calibration of probe 110. Signal generator 604 may provide commands for generating ultrasound signals. In an implementation, signal generator 604 may incorporate angular error values into signal timing and processing to compensate for mechanical alignment errors in probe 110.

Image generation module 610 may receive echo data from data collection module 600. Image generation module 610 may generate an ultrasound image based on the echo data and apply noise reduction and/or other pre-processing techniques to remove speckle and background noise from the image.

Error estimation module 620 may collect or identify offset parameter values for correcting distortion in images from image generation module 610. For example, based on known characteristics of target 310 (e.g., grid 410, checkerboard pattern 420, circles 430, etc.), distinctive characteristics in the ultrasound image of target 310 that may be associated with a cause of error may be identified. In one implementation, distortion identification may be done manually (e.g., based on visual observations) with error values entered by an operator and collected by error estimation module 620. In another implementation, error estimation module 620 may identify distortion. Distortion in the ultrasound image may include an inaccurate theta angle around theta axis 240, an inaccurate phi angle around axis 250, or a skewed transducer 210 that is not perpendicular to the intended scan plane, as characterized, for example, in images 520-540.

Error correction module 630 may receive and store offset parameter values from error estimation module 620. In one implementation, error correction module 630 may apply the stored offset parameter values to the simplified error model described above to generate distortion-free images (e.g., correcting for distortion) of target 310 during calibration. In another implementation, error correction module 630 may use the stored offset parameter values to correct images from patient ultrasound data (e.g., compensating for mechanical errors in probe 110).

Error correction module 630 may include an error model 632 and/or a distortion table 634. Error model 632 may include, for example, a theta rotation term, a phi rotation term, and a perpendicular error term as describe above in connection with FIG. 2. The stored offset parameter values may be applied to error model 632 to provide calibrated images from probe 110. In another implementation, error correction module 630 use a simpler table to correct probe 110 output without remapping an entire 3D ultrasound data set. For example, a typical bladder scanner uses a volume table to convert the detected bladder wall locations to a bladder volume number. Distortion table 634 may include a calculated value for an organ (e.g., a bladder, aorta, prostate, kidney, etc.) based on organ dimensions from ultrasound data as adjusted by error model 632. Thus, in this case, distortion table 634, particular to probe 110, could store specific "distorted" volumes or values to compensate for the mechanical errors in probe 110.

Figure 7:
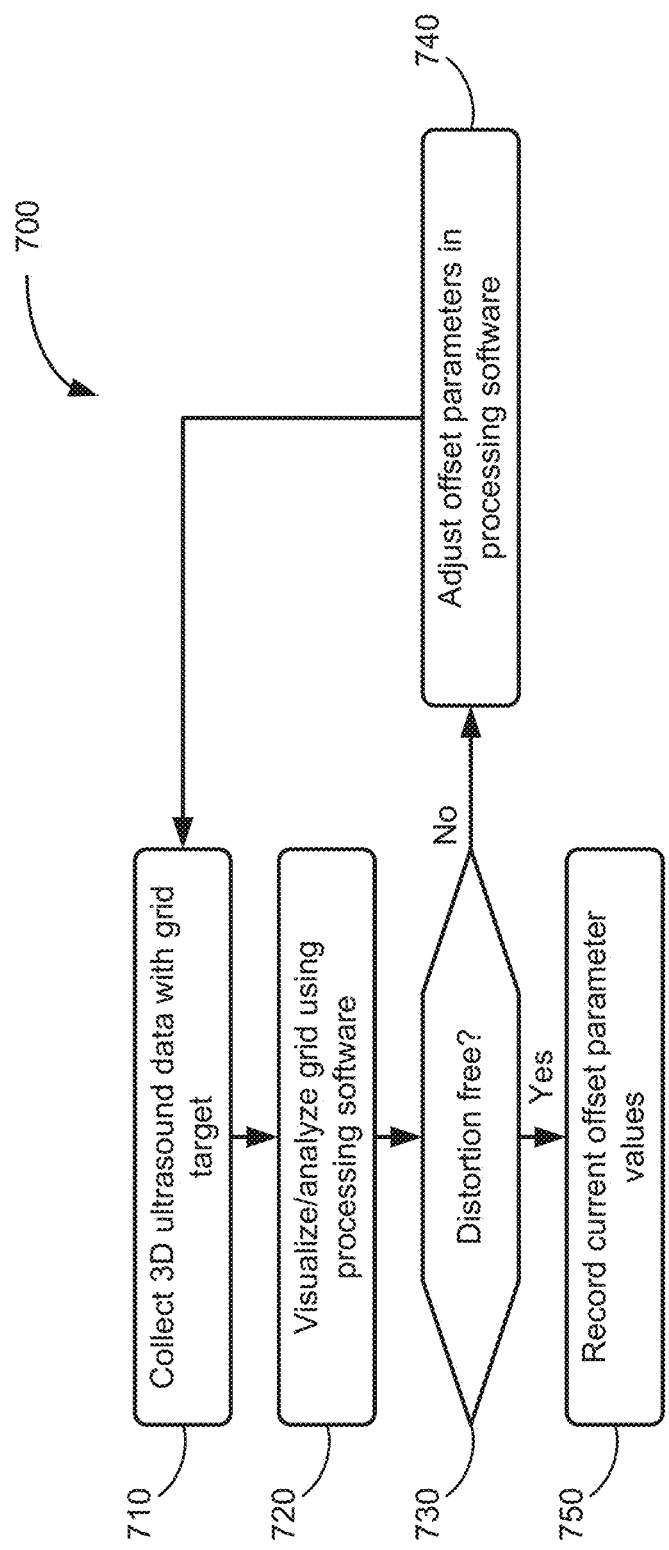
FIG. 7 is a process flow diagram for estimating probe error according to an implementation described herein.

FIG. 7 is a flow diagram illustrating exemplary process 700 for estimating probe error. Process 700 may be performed, for example, by probe 110. In another implementation, process 700 may be performed by probe 110 in conjunction with base unit 120 of system 100.

Process 700 may include collecting 3D ultrasound data of a grid target (block 710) and visualizing and/or analyzing the grid (block 720). For example, data collection module 600 may transmit ultrasound signals and collect echo data from target 310 in test fixture 300. Image generation module 610 may generate an ultrasound image (e.g., including a visual or non-visual representation) based on the echo data and apply noise reduction and/or other pre-processing techniques to remove speckle and background noise from the image. Image generation module 610 may calculate the 3D location of each sample point of the 3D ultrasound data using the scanline equation described above.

Process 700 may further include determining if the grid image is distortion free (block 730). For example, based on known characteristics of target 310, distinctive characteristics in the image that may be associated with a cause of error may be identified. In one implementation, offset parameter values may be collected from an operator based on visual observation. In another implementation, error estimation module 620 may determine estimated offset parameter values.

If the grid image is not distortion free (block 730—No), offset parameters may be adjusted in the processing software (block 740) and process 700 may return to block 710 to collect more data and visualize and/or analyze the grid using the adjusted offset parameters. For example, in one implementation, error parameters may be adjusted manually, with a user (e.g., a technician or operator) providing input into error estimation module 620 for one or more of a theta offset ($E_\theta$) value, a phi offset ($E_\phi$) value, and a perpendicular offset ($E_p$) value. In another implementation, error estimation module 620 may identify the theta offset ($E_\theta$) value, phi offset ($E_\phi$) value, or perpendicular offset ($E_p$) value. Image generation module 610 may apply the manually input or automatically generated offset parameters. When the offset parameters are correctly set, image generation module 610 maps each ultrasound sample point to the right location in 3D space. Thus, when using manual offset parameter input, the user/operator can adjust the offset parameters until the grid shape is normal without distortion. When using automatic error estimation, error estimation module 620 may optimize the offset parameters until the error is minimized between the error-compensated grid shape and the actual (e.g., ground truth) grid shape. In one implementation, conventional optimization methods could be applied (e.g., gradient descent, Newton method, Monte-Carlo search, etc.)

If the grid image is distortion free (block 730—Yes), the successful offset parameters may be recorded (block 750). For example, error estimation module 620 may pass the current offset parameters to error correction module 630 for storing and future use to automatically compensate for distortion in probe 110.

Figure 8:
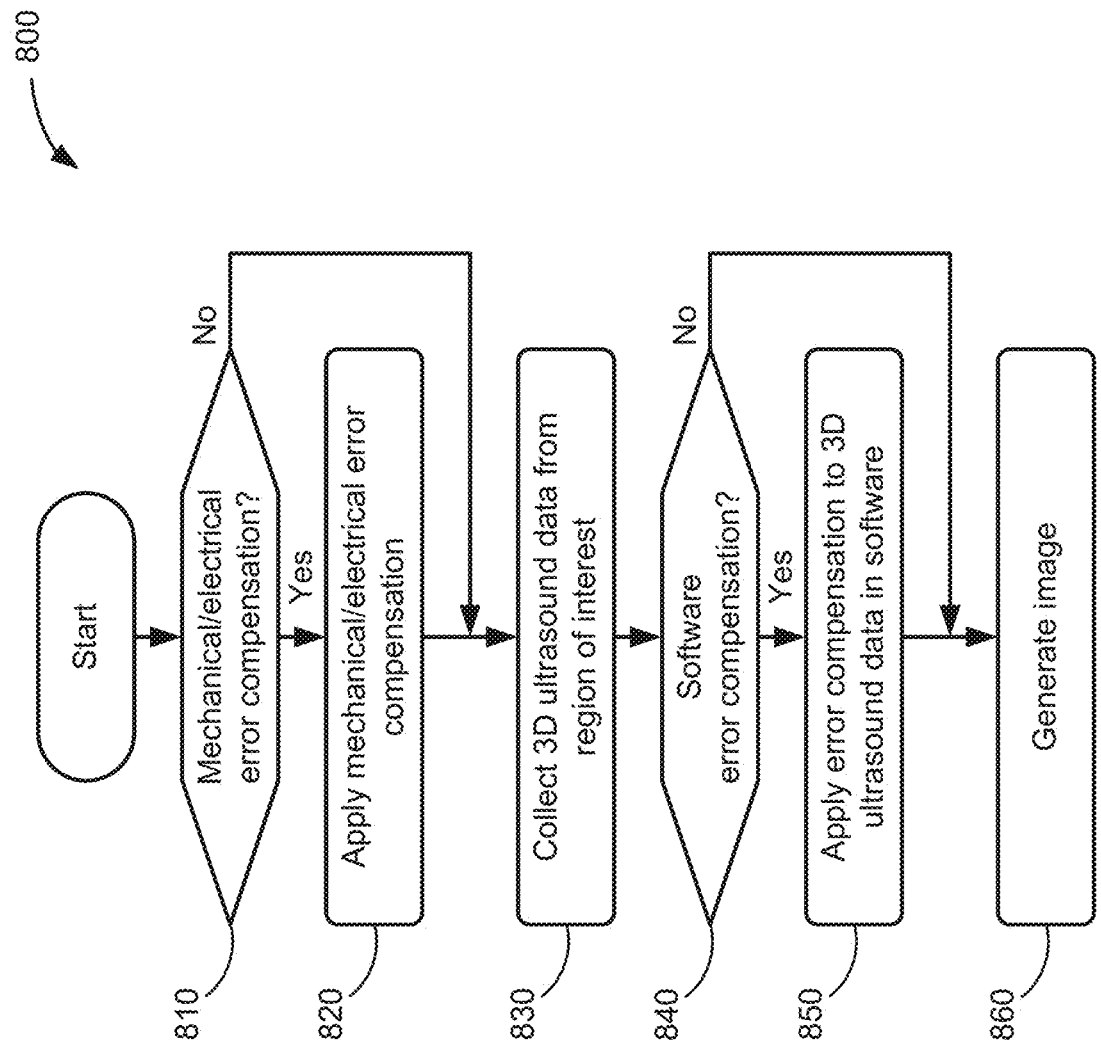
FIG. 8 is a process flow diagram for compensating for probe error according to an implementation described herein.

FIG. 8 is a flow diagram illustrating exemplary process 800 for compensating for probe error. Process 800 may be performed, for example, by probe 110. In another implementation, process 800 may be performed by probe 110 in conjunction with base unit 120 of system 100.

Process 800 may include determining if mechanical or electrical error compensation is applicable (block 810). For example, with the offset parameters stored in error correction module 630, different approaches to compensate for errors may be applied. In one implementation, probe 110 may be mechanically adjusted to compensate for errors at the time of 3D data collection. In another implementation, signals for angular rotation and/or pulse timing may be adjusted so that input values correspond to actual rotation angles in probe 110.

If mechanical or electrical error compensation is applicable (block 810—Yes), process 800 may include applying the mechanical or electrical error compensation (block 820). For example, skew angles in probe 110 (e.g., at the transducer 210/transducer bucket 215) can be physically adjusted to compensate for the measured perpendicular offset ($E_p$). In another implementation, to address phi offset ($E_\phi$) and theta offset ($E_\theta$), motor controller 602 or ultrasound pulse timing in signal generator 604 can be electronically adjusted for calibration.

If mechanical or electrical error compensation is not applicable (block 810—No) or after mechanical or electrical compensation is applied, process 800 may include collecting 3D ultrasound data from a region of interest (block 830) and determining if software error compensation is applicable (block 840). For example, an operator may use probe 110 to obtain a 3D ultrasound data of a region of interest of a patient. Error compensation for probe 110 may be configured to include software error compensation only or a combination of electrical/mechanical compensation and software compensation. In one implementation, system 100 can output distortion-free data from probe 110 using the same scanline calculations used in error measurement, without adjusting the hardware. Software error compensation values may be programmed into error correction module 630, for example, by including offset values for theta offset ($E_\theta$), phi offset ($E_\phi$), and/or perpendicular offset ($E_p$). According to another implementation, system 100 can use a simple method to correct a final output without remapping the entire 3D ultrasound data set. For example, a typical bladder scanner uses a volume table to convert the detected bladder wall locations to a bladder volume number. In this case, each probe device 110 could have a specific 'distorted' volume table (e.g., stored in error correction module 630) to compensate the mechanical errors in the probe.

If software error compensation is applicable (block 840—Yes), process 800 may include applying the error compensation to the 3D ultrasound data via software (block 850). For example, in one implementation, error correction module 630 may use offset values for theta offset ($E_\theta$), phi offset ($E_\phi$), and/or perpendicular offset ($E_p$) to remap the 3D ultrasound data set. In another implementation, error correction module 630 may apply a corrected volume table, specific to probe 110, to identify compensated values for a region or organ of interest.

If software error compensation is not applicable (block 840—No) or after software error compensation is applied, process 800 may include generating a compensated output (block 860). For example, in one implementation error correction module 630 may generate an ultrasound image of the region of interest with remapped data. In another implementation, error correction module 630 may provide an output value (such as a volume estimate, diameter estimate, width/height estimate, etc.) based on a pre-calculated distortion table (e.g., distortion table 634).

FIG. 9A is a simplified schematic of probe 110 with a test fixture 900. FIG. 9B is a simplified exploded view of test fixture 900. Typically, an ultrasound calibration test requires use of a large target immersed in water or placed inside a tissue-mimicking material (referred to as a phantom). For example, a typical probe 110 may have up to 120 degree phi rotation about axis 250 (FIG. 2), which may require a target size of at least six-by-six inches (approximately 15-by-15 centimeters) and a depth of more than four inches. Thus, a typical test fixture can take up valuable space in, for example, a cart for system 100.

Referring collectively to FIGS. 9A and 9B, the repetitiveness of the grid-like target pattern in target 310 allows test fixture to be miniaturized using acoustic mirrors. Particularly, metal reflectors 910 (e.g., an acoustic mirror) may be used as walls for test fixture 900, forming an open cavity therein. In one implementation, a reflector 915 (e.g., another acoustic mirror) may be used as a base of test fixture 900 to give the appearance of more depth. Target 310 may be anchored to reflectors 910 or suspended/inserted in a tissue-mimicking material 920. In one implementation, as shown in FIG. 9B, target 310 may be positioned at a mid-span position of reflectors 910 and parallel to reflector 915.

When exposed to ultrasonic energy, reflectors 910 and 915 may generate repetitive patterns of target 310, thus giving a representation of a larger test fixture to probe 110. According to implementations described herein, the size of target 310 and the corresponding side dimensions, S, of test fixture 900 may be less than four inches, and preferably about two inches. The depth of test fixture, D, may be less than four inches, and preferably between two and three inches. Thus, a significant reduction in test fixture space can be realized over conventional calibration test fixtures.

Figure 10:
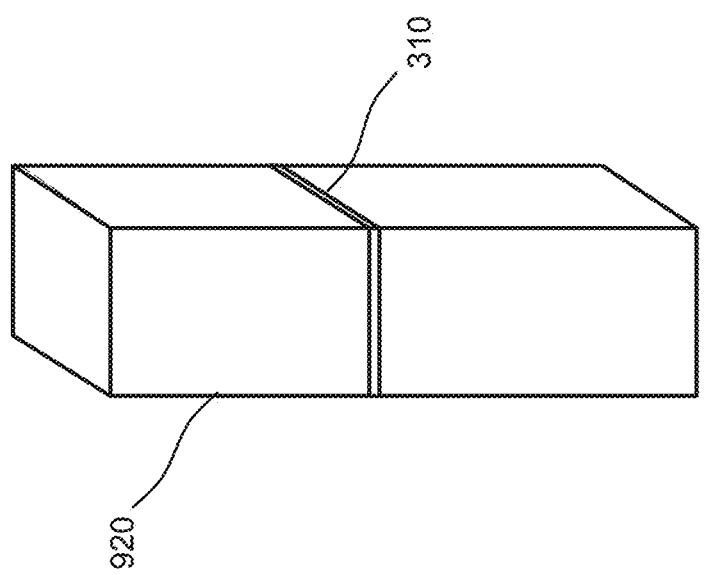
FIG. 10 is a simplified diagram illustrating another test fixture according to another implementation described herein.

FIG. 10 is a simplified schematic another test fixture 1000. Test fixture 1000 includes tissue-mimicking material 920 and target 310. In the embodiment of FIG. 10, tissue-mimicking material 920 may include rubber material (or another solid material) with target 310 embedded therein. A rubber-air interface provides a good echo reflector due to high acoustic impedance mismatching. Thus, when tissue-mimicking material 920 is made of rubber (or another material that provides high acoustic impedance mismatching), the rubber-air interface can effectively reflect echoes (from/to probe 110) without using separate walls (such as reflectors 910) or a base (such as reflector 915).

Figure 11:
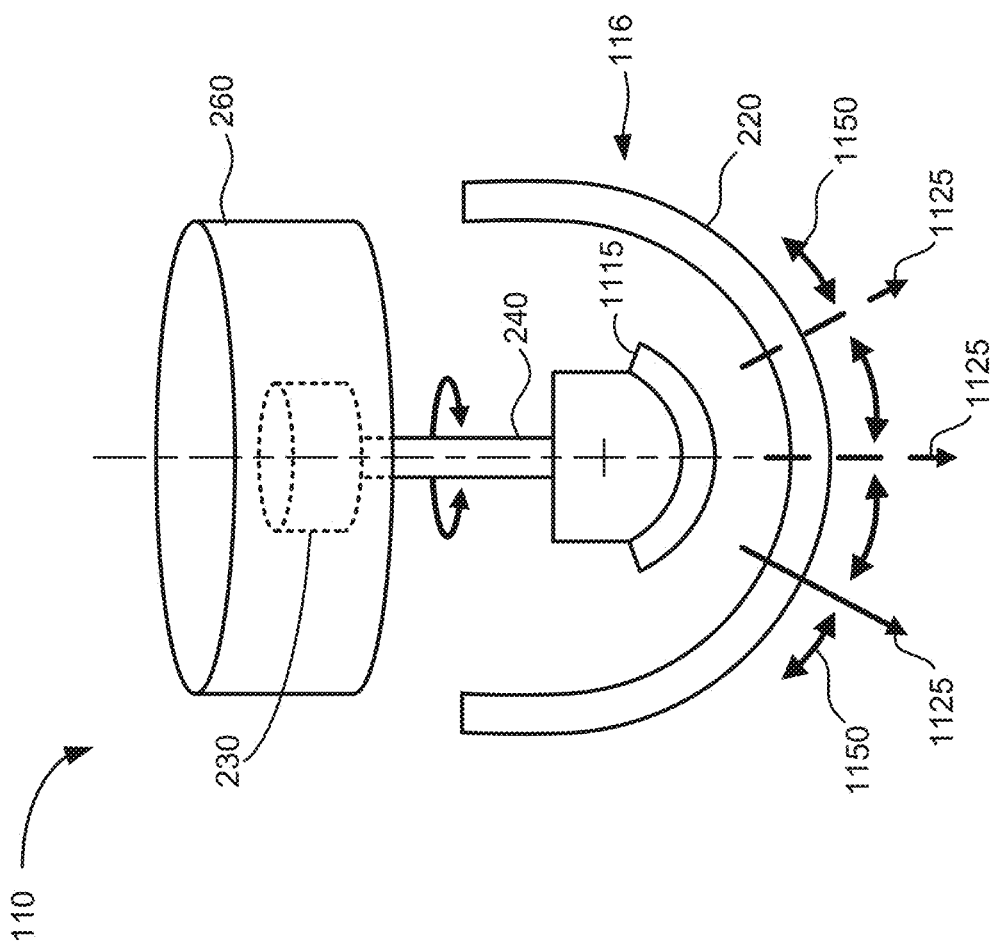
FIG. 11 is a schematic of a portion of the probe of FIG. 1 according to another implementation.

FIG. 11 is a schematic of a portion of the probe 110 according to another implementation. In the configuration of FIG. 11, probe 110 includes an array transducer 1115. Array transducer 1115 may include a curved array (e.g., as shown in FIG. 11) or a linear array. Array transducer 1115 may provide an ultrasonic beam 1125 that may be tilted in the phi direction 1150 without a motor (e.g., without motor 235). Similar to motor 235 of FIG. 2, array transducer 1115 may be mounted for theta rotation around axis 240. The configuration of probe 110 in FIG. 11 may have some different caused of angular error than the configuration of FIG. 2. The same or similar simplified error model of angular errors (E) inside probe 110 can be approximated as the combination of three sources: a theta offset ($E_\theta$) associated with theta axis 240, a phi offset ($E_\phi$) associated with phi direction 1150, and a perpendicular offset ($E_p$) associated with a skew angle perpendicular to the scan plane, where the scan plane varies with the change in phi direction of beam 1125 from array transducer 1115.

FIG. 12 is a block diagram illustrating exemplary physical components of base unit 120. Base unit 120 may include a bus 1210, a processor 1220, a memory 1230, an input component 1240, an output component 1250, and a communication interface 1260.

Bus 1210 may include a path that permits communication among the components of valve controller 150. Processor 1220 may include a processor, a microprocessor, or processing logic that may interpret and execute instructions. Memory 1230 may include any type of dynamic storage device that may store information and instructions (e.g., software 1235), for execution by processor 1220, and/or any type of non-volatile storage device that may store information for use by processor 1220.

Software 1235 includes an application or a program that provides a function and/or a process. Software 1235 is also intended to include firmware, middleware, microcode, hardware description language (HDL), and/or other form of instruction.

Input component 1240 may include a mechanism that permits a user to input information to base unit 120, such as a keyboard, a keypad, a button, a switch, a touch screen, etc. Output component 1250 may include a mechanism that outputs information to the user, such as a display, a speaker, one or more light emitting diodes (LEDs), etc.

Communication interface 1260 may include a transceiver that enables base unit 120 to communicate with other devices and/or systems via wireless communications, wired communications, or a combination of wireless and wired communications. For example, communication interface 1260 may include mechanisms for communicating with another device or system, such as probe 110, via a network, or to other devices/systems, such as a system control computer that monitors operation of multiple base units (e.g., in a hospital or another type of medical monitoring facility). In one implementation, communication interface 1260 may be a logical component that includes input and output ports, input and output systems, and/or other input and output components that facilitate the transmission of data to/from other devices.

Base unit 120 may perform certain operations in response to processor 1220 executing software instructions (e.g., software 1235) contained in a computer-readable medium, such as memory 1230. A computer-readable medium may be defined as a non-transitory memory device. A non-transitory memory device may include memory space within a single physical memory device or spread across multiple physical memory devices. The software instructions may be read into memory 1230 from another computer-readable medium or from another device. The software instructions contained in memory 1230 may cause processor 1220 to perform processes described herein. Alternatively, hardwired circuitry, such as an application-specific integrated circuit (ASIC), a field-programmable gate array (FPGA), etc., may be used in place of or in combination with software instructions to implement processes described herein. Thus, implementations described herein are not limited to any specific combination of hardware circuitry and software.

Base unit 120 may include fewer components, additional components, different components, and/or differently arranged components than those illustrated in FIG. 12. As an example, base unit 120 may include one or more switch fabrics instead of, or in addition to, bus 1210. Additionally, or alternatively, one or more components of base unit 120 may perform one or more tasks described as being performed by one or more other components of base unit 120.

Systems and methods described herein allow for calibration of 3D ultrasound probes in a computationally-efficient manner using targets that include a repetitive pattern along two axes and a simplified error model. Offset parameter values can be determined based on comparison of calibration tests images with simple grid-like target shapes. In one implementation, systems and methods described herein may be performed during on-site quality control tests. If calibration errors are detected, the offset parameter values can be applied using hardware or software changes to compensate for mechanical alignment errors in the probe. As an example, the offset parameter values may be used by a service technician for calibration. In another example, offset parameter values may be incorporated into software (e.g., software 1235) via on-site or remote (e.g., network) interactions.

The simplified error model, along with use of the targets having repetitive patterns, also allows for probe calibration with smaller test fixtures. In some cases, the test fixtures may use reflective walls or eliminate walls entirely.

The foregoing description of exemplary implementations provides illustration and description, but is not intended to be exhaustive or to limit the embodiments described herein to the precise form disclosed. Modifications and variations are possible in light of the above teachings or may be acquired from practice of the embodiments.

Although the invention has been described in detail above, it is expressly understood that it will be apparent to persons skilled in the relevant art that the invention may be modified without departing from the spirit of the invention. Various changes of form, design, or arrangement may be made to the invention without departing from the spirit and scope of the invention.

No element, act, or instruction used in the description of the present application should be construed as critical or essential to the invention unless explicitly described as such. Also, as used herein, the article "a" is intended to include one or more items. Further, the phrase "based on" is intended to mean "based, at least in part, on" unless explicitly stated otherwise.

Use of ordinal terms such as "first," "second," "third," etc., in the claims to modify a claim element does not by itself connote any priority, precedence, or order of one claim element over another, the temporal order in which acts of a method are performed, the temporal order in which instructions executed by a device are performed, etc., but are used merely as labels to distinguish one claim element having a certain name from another element having a same name (but for use of the ordinal term) to distinguish the claim elements.

What is claimed is:

1. A method for calibrating an ultrasound probe, the method comprising:
   receiving, from the ultrasound probe, data of a target within a test fixture, wherein the target includes a repetitive pattern along two axes;
   generating a first ultrasound image of the target;
   identifying distortion of the target in the first ultrasound image;
   estimating, based on the identifying, offset parameter values for one or more angular errors within the ultrasound probe;
   generating a second ultrasound image of the target using the offset parameter values;
   identifying corrected distortion of the target in the second ultrasound image; and
   storing the offset parameter values.

2. The method of claim 1, further comprising:
   after the estimating, applying the one or more angular errors to an error model for the ultrasound probe.

3. The method of claim 1, wherein the one or more angular errors include:
   a first angular error relative to a first axis of the probe extending in a longitudinal direction,
   a second angular error relative to a second axis extending in a direction orthogonal to the first axis, and
   a third error indicating a skew angle from perpendicular relative to a scan plane.

4. The method of claim 3, wherein identifying distortion of the target in the first ultrasound image includes detecting rotation of the target in the first ultrasound image.

5. The method of claim 3, wherein identifying distortion of the target in the first ultrasound image includes one or more of detecting a discontinuity of the target in the first ultrasound image or detecting local expansion or contraction of the target in the first ultrasound image.

6. The method of claim 3, wherein identifying distortion of the target in the first ultrasound image includes detecting skewed patterns on the target in the first ultrasound image.

7. The method of claim 1, further comprising:
   applying mechanical error compensation techniques to the ultrasound probe based on the stored offset parameter values; or
   applying electrical error compensation techniques to the ultrasound probe based on the stored offset parameter values.

8. The method of claim 1, further comprising:
   collecting, after the storing, ultrasound data from a region of interest; and
   applying error compensation to the ultrasound data based on the stored offset parameter values.

9. The method of claim 1, wherein the test fixture includes reflectors that, when exposed to ultrasonic energy, generate repetitive patterns of the target.

10. The method of claim 1, wherein the target is embedded in a material within the test fixture.

11. The method of claim 10, wherein the material includes a solid material, and wherein the three-dimensional data of the target within the test fixture includes echo data from a solid material-air interface.

12. A device, comprising:
   a communication interface;
   a memory device for storing instructions; and
   a processor configured to execute the instructions to:
      receive, from an ultrasound probe, data of a target within a test fixture, wherein the target includes a repetitive pattern along two axes;
      generate a first ultrasound image of the target;
      identify distortion of the target in the first ultrasound image;
      estimate, based on the identifying, offset parameter values for one or more angular errors within the ultrasound probe;
      generate a second ultrasound image of the target using the offset parameter values;
      identify corrected distortion of the target in the second ultrasound image; and
      store the offset parameter values.

13. The device of claim 12, wherein the processor is further configured to execute the instructions to:
   apply, after the estimating, the one or more angular errors to an error model for the ultrasound probe.

14. The device of claim 13, wherein the processor is further configured to execute the instructions to:
   collect, after the storing, ultrasound data from a region of interest;
   apply error compensation to the ultrasound data using the error model and the stored offset parameter values; and
   generate an ultrasound image of the region of interest based on the error compensation.

15. The device of claim 12, wherein the ultrasound probe includes one of a single element transducer or an annular transducer array that rotates about two different axes.

16. The device of claim 12, wherein the ultrasound probe includes one of a linear transducer array or curved transducer array that rotates about a longitudinal axis.

17. The device of claim 12, wherein a top surface area of the target is less than sixteen square inches.

18. The device of claim 12, wherein three-dimensional data of a target is collected from the target immersed in one of water, gel, or solid material within the test fixture.

19. A non-transitory computer-readable medium containing instructions executable by at least one processor, the computer-readable medium comprising one or more instructions to:
   receive, from an ultrasound probe, three-dimensional data of a target within a test fixture, wherein the target includes a repetitive pattern along two axes;
   generate a first ultrasound image of the target;
   identify distortion of the target in the first ultrasound image;
   estimate, based on the identifying, offset parameter values for one or more angular errors within the ultrasound probe;
   generate a second ultrasound image of the target using the offset parameter values;
   identify corrected distortion of the target in the second ultrasound image; and
   store the offset parameter values.

20. The non-transitory computer-readable medium claim 19, wherein the angular errors include a first angular error relative to a first axis of the probe extending in a longitudinal direction, a second angular error relative to a second axis extending in a direction orthogonal to the first axis, and a third error indicating a skew angle from perpendicular relative to a scan plane; and wherein the instructions further comprise one or more instructions to:
   collect, after the storing, ultrasound data from a region of interest; and
   apply error compensation to the ultrasound data based on the stored offset parameter values.

* * * * *